US009833608B2

(12) United States Patent
Masson

(10) Patent No.: US 9,833,608 B2
(45) Date of Patent: Dec. 5, 2017

(54) POSITIONING METHODS FOR INTRAVASCULAR ELECTRODE ARRAYS FOR NEUROMODULATION

(71) Applicant: NeuroTronik IP Holding (Jersey) Limited, St. Helier (JE)

(72) Inventor: Stephen C Masson, Raleigh, NC (US)

(73) Assignee: NeuroTronik IP Holding (Jersey) Limited, St. Helier (JE)

(\*) Notice: Subject to any disclaimer, the term of this patent is extended or adjusted under 35 U.S.C. 154(b) by 34 days.

(21) Appl. No.: 14/085,773

(22) Filed: Nov. 20, 2013

(65) Prior Publication Data

US 2014/0142590 A1 May 22, 2014

Related U.S. Application Data

(60) Provisional application No. 61/728,796, filed on Nov. 20, 2012, provisional application No. 61/728,799, filed on Nov. 20, 2012, provisional application No. 61/728,805, filed on Nov. 20, 2012.

(51) Int. Cl.
| | |
|---|---|
| *A61B 19/00* | (2006.01) |
| *A61N 1/05* | (2006.01) |
| *A61N 1/39* | (2006.01) |
| *A61N 1/36* | (2006.01) |

(52) U.S. Cl.
CPC ............ *A61N 1/05* (2013.01); *A61N 1/056* (2013.01); *A61N 1/36053* (2013.01); *A61N 1/36128* (2013.01); *A61N 1/3962* (2013.01)

(58) Field of Classification Search
CPC ...... A61N 1/3627; A61N 1/3684; A61N 1/05; A61N 1/36578; A61N 1/36535; A61N 1/0558; A61N 1/36128; A61N 1/056; A61N 1/13956; A61B 5/0452; A61B 5/0538; A61B 5/0402; A61B 5/0408; A61B 5/0472; A61B 5/04012; A61B 5/489; A61B 5/0037; A61B 2562/0209; A61B 19/5225; A61B 17/3468; A61M 2230/04
USPC ........................................................ 606/129
See application file for complete search history.

(56) References Cited

U.S. PATENT DOCUMENTS 4,809,681 A \* 3/1989 Kantrowitz et al. ............ 600/17

\* cited by examiner

*Primary Examiner* — Melanie Tyson

(57) ABSTRACT

A method for positioning an electrode array of a neuromodulation catheter at a target circumferential position along a posterior wall of a superior vena cava includes advancing the catheter to a target longitudinal position within the superior vena cava, and orienting a marker on the extracorporeal portion of the catheter in a circumferential orientation known to position the array at the target circumferential position along the posterior wall. A method of positioning the array at a target longitudinal position includes advancing the catheter into the superior vena cava and using features of the catheter to detect the location of right atrial tissue, such as by sensing for a P-wave using an electrogram captured using an electrode carried at a distal end of the catheter, or by using such electrodes to capture the atrium using atrial pacing pulses. Once the location of the right atria is determined, the electrode array may be deployed in a position known to be proximal to the atrium.

4 Claims, 5 Drawing Sheets

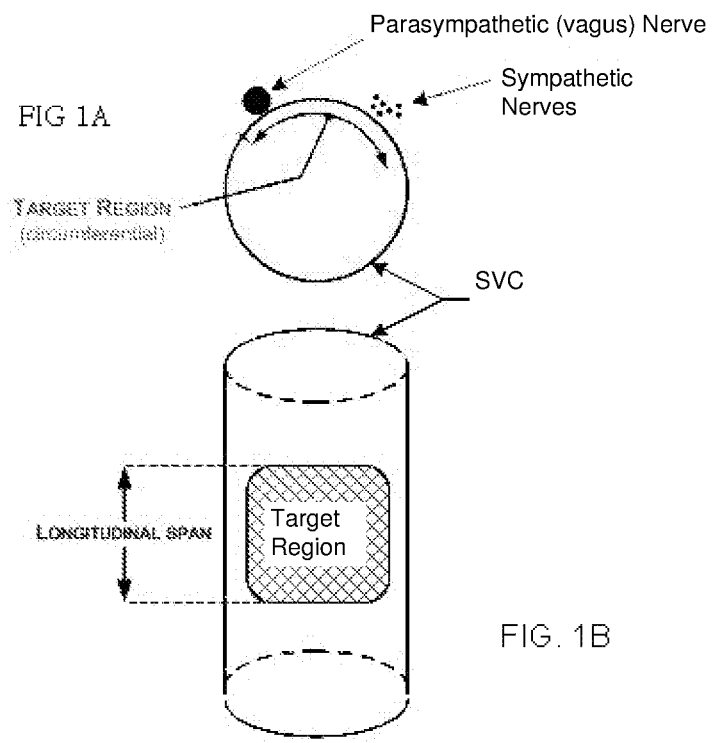
FIG 1A
FIG. 1B
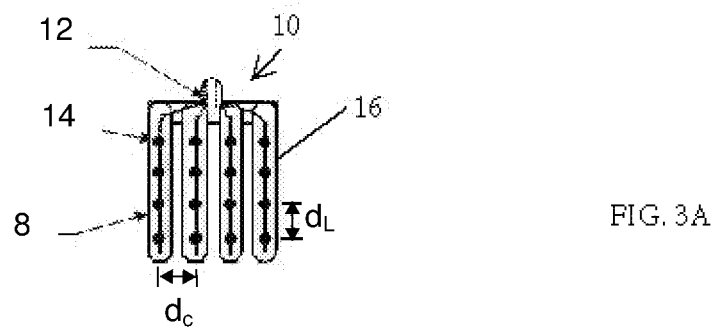
FIG. 3A

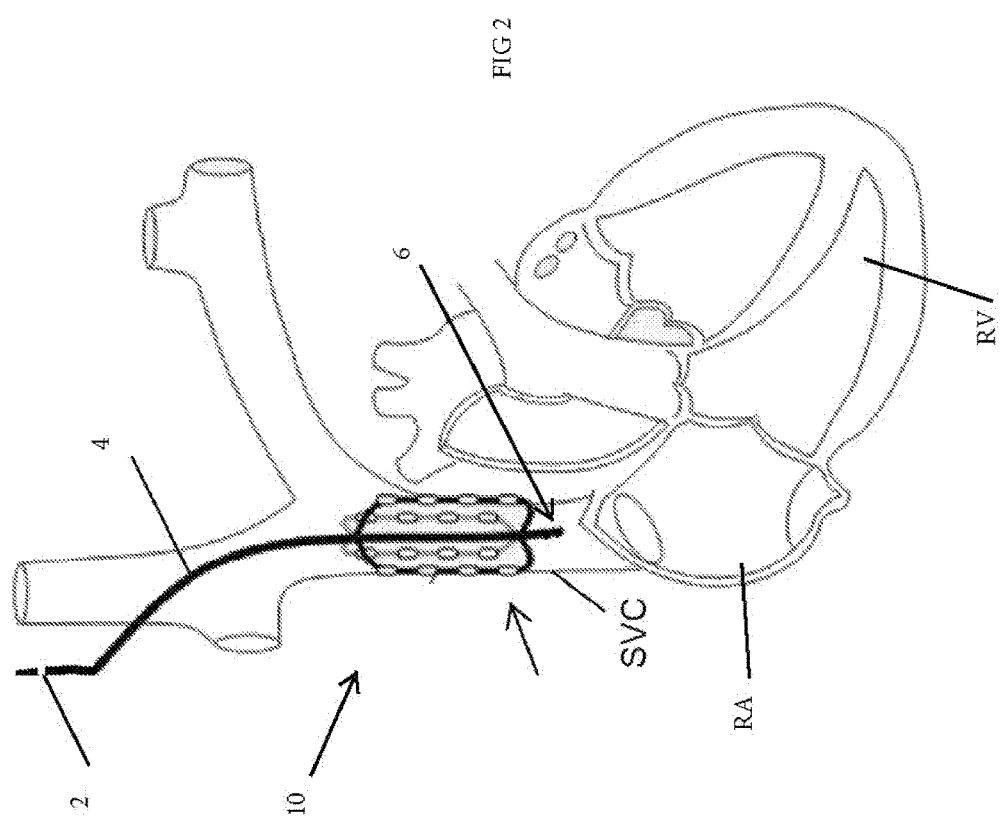

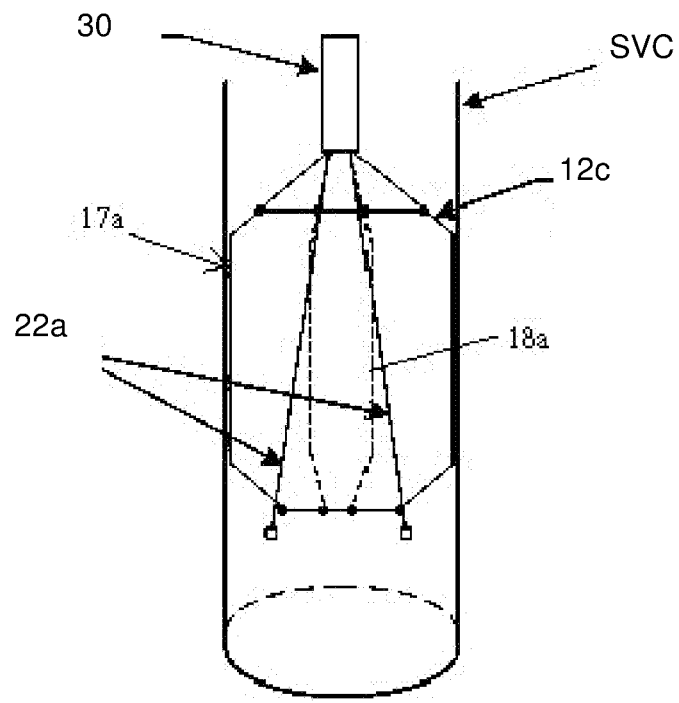
FIG 7
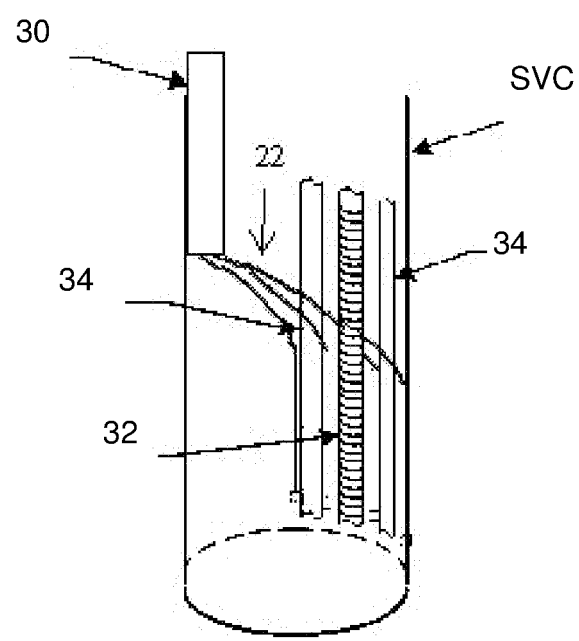

US 9,833,608 B2

POSITIONING METHODS FOR INTRAVASCULAR ELECTRODE ARRAYS FOR NEUROMODULATION

This application claims the benefit of the following U.S. Provisional Applications, each of which was filed Nov. 20, 2012 and each of which is incorporated herein by reference: U.S. 61/728,796, U.S. 61/728,799, and U.S. 61/728,805.

TECHNICAL FIELD OF THE INVENTION

The present application generally relates to intravascular electrode arrays for use in neuromodulation. More particularly, the application relates to electrode supports used to position the intravascular electrodes against the interior wall of a blood vessel and methods used to position the electrode supports.

BACKGROUND

Prior applications filed by an entity engaged in joint research with the owner of the present application describe neuromodulation methods using electrodes positioned in a blood vessel. The electrodes disposed inside the blood vessel are energized to stimulate or otherwise modulate nerve fibers or other nervous system targets located outside the blood vessel. Those prior applications include U.S. Publication No. 2007/0255379, entitled Intravascular Device for Neuromodulation, U.S. 2010/0023088, entitled System and Method for Transvascularly Stimulating Contents of the Carotid Sheath, U.S. application Ser. No. 13/281,399, entitled Intravascular Electrodes and Anchoring Devices for Transvascular Stimulation, International Application PCT/US12/35712, entitled Neuromodulation Systems and Methods for Treating Acute Heart Failure Syndromes, and U.S. application Ser. No. 13/547,031 entitled System and Method for Acute Neuromodulation, filed Jul. 11, 2012. Each of these applications is attached in the Appendix and is fully incorporated herein by reference. The latter application describes a system which may be used for hemodynamic control in the acute hospital care setting, by transvascularly directing therapeutic stimulus to parasympathetic nerves and/or sympathetic cardiac nerves using an electrode array positioned in the superior vena cava (SVC).

Proper placement of intravascular electrodes is essential for neuromodulation. The electrodes must be positioned to capture the target nerve fibers, while avoiding collateral stimulation of non-target nerve fibers. Mapping procedures are typically performed at the time of electrode placement to identify the optimal electrode location. Mapping can be manually controlled by the clinician or automatically controlled by the neuromodulation system. During mapping, different electrodes, combinations of electrodes, or arrays can be independently energized while the target response to the stimulus is monitored. For stimulation relating to cardiac or hemodynamic function, parameters such as heart rate, blood pressure, venticular inotropy and/or cardiac output might be monitored. In some cases mapping includes additional steps of repositioning the electrode carrying member so as to allow additional electrode sites to be sampled. The mapping process is performed until the optimal electrode or combination of electrodes for the desired therapy array is identified.

Referenced prior application Ser. No. 13/547,031 describes a neuromodulation system that may be used for hemodynamic control in the acute hospital care setting, by transvascularly directing therapeutic stimulus to parasympathetic nerves and/or sympathetic cardiac nerves using an electrode array positioned in the SVC. That system includes a control system suitable for carrying out the therapy. The neuromodulation system includes a therapeutic catheter having therapeutic elements such as electrode arrays, and optionally, patient and system diagnostic elements; sensors (e.g. pressure sensors, flow sensors, other hemodynamic sensors, other patient condition sensors, and system condition sensors such as position sensors, system connection sensors or other system error condition monitoring sensors). The neuromodulation system also includes an external stimulator, (also referred to here as a neuromodulator or "NM"). The external stimulator has a clinician user interface and functions to provide therapeutic stimulation outputs to the therapeutic catheter; therapeutic outputs that are dynamically controlled in a closed-loop manner in response to information from one or more of the diagnostic elements, or may be controlled manually by the clinician. The diagnostic elements include sensors for patient hemodynamic feedback such as heart rate (HR), blood pressure (BP), and other suitable sensed or derived hemodynamic parameters (which may include central venous pressure (CVP), pulmonary capillary wedge pressure (PCWP), cardiac index, derivations of vascular resistance, cardiac output, and cardiac filling pressures); sensors and/or analyzers to determine other patient conditions such as cardiac arrhythmia, cardiac capture, respiration, or patient movement; and other sensors and analyzers to monitor system conditions for error, malfunction or unsafe state (referred to as "safety monitoring") that should be indicated to the clinician and/or result in termination of stimulation.

During use of such systems for hemodynamic control, the electrodes are positioned at the distal end of an intravascular catheter (referenced here as the "neurocatheter" or "NC") percutaneously delivered to the target stimulation site within the SVC. The electrodes are placed against the SVC wall in order to transvascularly stimulate parasympathetic and sympathetic cardiac nerves. Prior studies have identified areas on the posterior wall of the mid-to-cranial SVC, between the brachiocephalic junction and right atrium, where both parasympathetic and sympathetic nerves can be electrically stimulated. The use of an array of electrodes on the NC allows general placement into a target region of the SVC without a requirement for precise placement. The NC electrode array only needs to be placed into this general SVC target region to facilitate neuromodulation system function. This region can be defined by both a longitudinal range of the SVC, and by a circumferential range of the SVC (see FIGS. 1A and 1B). Previous disclosures have identified the preferred longitudinal range as the mid-to-cranial SVC, and preferred circumferential range along the posterior side of the SVC.

It is known that accessing the human SVC using the widely accepted, standard percutaneous procedure, especially from venous access sites such as the internal jugular, subclavian or femoral veins is a simple and straightforward technique, in which a variety of clinicians are proficient. In order to provide for both ease-of-use in the acute hospital setting and allow for positioning without the use of imaging, such as fluoroscopy, the NC contains an "array" of electrodes to provide a coverage area for capture of target cardiac nerves. All of the electrodes in the array can then be connected to the NM, and the NM can then "select" the desired anodes and cathodes by means of electronic switching circuitry in its response mapping function.

BRIEF DESCRIPTION OF THE DRAWINGS

FIG. 1A is a top, cross-section view of the superior vena cava (SVC) illustrating a target electrode region for delivery of therapy to parasypathetic and sympathetic targets.

FIG. 1B is an anterior view of the SVC illustrating the target region depicted in FIG. 1A.

FIG. 2 schematically illustrates an exemplary neurocatheter positioned within the SVC.

FIGS. 5, 6 and 7 are elevation views of first, second and third support structures on catheter bodies. The support structures are schematically shown disposed within a blood vessel with the portion of the support structure that carries the electrode arrays (not shown) biased against the wall of the blood vessel.

FIG. 8 illustrates positioning of a support structure in a blood vessel within which cardiac rhythm management leads have been previously positioned.

DETAILED DESCRIPTION

Figure 3B:
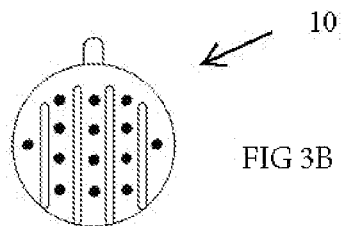
FIGS. 3A. 3B, 4A and 4B are plan views illustrating second, third, and fourth embodiments, respectively, of electrode arrays.

The present application describes methods that may be used to select a deployment site for the neurocatheter's electrode array within the SVC. Certain disclosed methods include steps selected to ensure that the identified deployment site places the electrodes where they will capture the target nerve structures during application of therapy. In the illustrated examples, the target nerve structures are both cardiac sympathetic nerves and parasympathetic nerve targets such as the vagus nerve, but the disclosed methods may be used to select deployment sites intended to capture one or the other of such nerve targets (parasympathetic or sympathetic). The present application also describes methods that may be used to select a deployment site within the SVC that will place the electrodes a safe distance from the cardiac tissue of the atria, so as to avoid unintended atrial capture during application of therapy. Finally, methods are disclosed for identifying which electrodes in an electrode array are likely positioned over cardiac rhythm management (CRM) leads also disposed in the SVC, so that alternative electrode pairs may be used for the neuromodulation therapy.

NeuroCatheter Positioning During Placement

As described earlier, a preferred method of placement of the NC involves deployment of the electrode array into a target region of the SVC, but does not necessarily require precise placement. This general targeting, together with the neuromodulation system's automatic mapping response algorithm to determine which electrodes within the array produce the optimal therapeutic response, allows placement of the NC with imaging guidance, typically fluoroscopy, or without any imaging. It is advantageous to place the NC without fluoroscopy because it minimizes radiation exposure to the patient and clinician, reduces procedure time, cost, and special hospital settings that are required for image-guided procedures. Placing the NC correctly without imaging requires the NC be positioned correctly in the SVC in both the circumferential and longitudinal directions.

Placing Electrodes at Target Circumferential Position Within SVC

The first method described is for placement of the NC into the target region without the use of imaging. More particularly, this method allows the electrode array to be positioned in the correct circumferential position within the SVC using an electrode array that will not extend the full circumference of the SVC. This method utilizes a neurocatheter having a circumferential marker visible from the exterior of the NC (e.g. a marker on the portion of the neurocatheter shaft that remains outside of the body during therapy) that corresponds to the mid-anterior position. See, e.g., FIG. 2 which illustrates a neurocatheter 10 having a marker 2 positioned on the neurocatheter body 4 disposed outside the patient. By aligning this marker perpendicular to the supine patient, the electrode array in the NC will deploy to cover the preferred circumferential range on the posterior wall (i.e. the "target region" identified in FIG. 1A). The electrode array and support structure would be manufactured in a fixed orientation with respect to the marker on the NC body. This marker can be a stripe, line or a color coded mark and labeled accordingly.

Placing Electrodes at Target Longitudinal Position Within SVC

An embodiment for determining correct longitudinal NC placement is by electrical identification of the position of the right atrium. A neurocatheter positioned using this technique might be one having a set of orthogonal or ring electrodes, suitable for floating atrial sensing and/or pacing, on its distal end. See, for example, ring electrodes 6 in FIG. 2. In one method that uses atrial sensing, the NC is slowly inserted while the neuromodulator displays the sensed electrogram signal. The clinician advances the NC until atrial intracardiac electrical activity (P-waves) is displayed. Once P-waves are displayed, it is known that the NC distal tip is just inside the right atrium (RA). At this point, the NC is pulled back a fixed distance (preferably 1.5 cm) from 1 to 4 cm into the SVC by using graduated markings on the NC body or by handle design. Once pulled back, the electrode array can be deployed (into the position shown in FIG. 2) and will be in the correct longitudinal region.

In another method, atrial pacing is used to identify the location of the right atrium. As the NC is advanced, the clinician enables one or a series of pacing pulses above typical atrial capture thresholds synchronized to the patient's cardiac rhythm (as detected from the neuromodulation system's ECG detection function previously disclosed). The clinician advances the NC until atrial capture is detected, indicating the right atrium has been reached. In one preferred embodiment, the neuromodulator automatically determines atrial capture by signal processing looking for the evoked response as a result of the pacing pulse. In another embodiment, the clinician detects atrial capture from the displayed ECG. In either case, the identification of the location of the right atrium is used as previously described to identify longitudinal position, where the NC is pulled back as described previously and the NC electrode array deployed.

Another preferred embodiment uses an inner lead extendable from the neurocatheter. This lead includes a set of orthogonal or ring electrodes suitable for floating atrial sensing and/or pacing. For example, the lead supporting electrodes 6 shown in FIG. 2 would be extendable as described in this paragraph. Once the NC has been inserted into the SVC, the clinician fully extends the atrial "floating lead" from the NC using a handle at the proximal end of the NC. The floating lead, when fully extended, represents a known, appropriate distance (preferably 1.5 cm) from the distal edge of the deployed NC electrode array. Using the atrial sensing method as described above, the NC is slowly inserted while the NM displays the sensed electrogram signal. Once P-waves are displayed, the distance from the right atrium to the distal edge of the NC electrode array, once deployed, is known. At this point, the electrode array can be deployed and will be in the correct longitudinal region. Alternatively, the atrial pacing method described above can be used with this embodiment. More specifically, as the NC is advanced with its extended "floating lead", the clinician enables one or a series of pacing pulses as described earlier. The clinician advances the NC until atrial capture is detected, indicating the right atrium has been reached. In either case, the identification of the location of the right atrium is used as previously described to identify longitudinal position and safely deploy the NC electrode array.

Another preferred embodiment to facilitate longitudinal placement is by measured distance from the venous access site to the mid-to-cranial SVC and use of graded markers, similar to a ruler, on the shaft of the neurocatheter. A relative measurement device (similar to a tape measure) is used to "measure" the distance from the entry site (jugular, subclavian, or femoral vein) to an anatomic mark on the surface of the patient's chest. Then the NC is introduced and inserted until the corresponding marker on the NC body is aligned with the introducer sheath entry site. For example, the typical distance from the jugular or subclavian vein entry site to the right atrial-SVC junction is 16.5 cm. The tape measure could be used to measure from the entry site to an anatomic landmark, such as the sternum. A relative marker that corresponds to 1-2 cm short of the right atrium (equivalent to a NC depth of 14.5 to 15.5 cm) is used to determine the proper insertion depth for the clinician.

In addition to the above-described methods, if desired, the NC can be placed in the correct circumferential and longitudinal orientation is by using fluoroscopic imaging. The NC will have radiopaque materials on both the NC body to facilitate longitudinal positioning prior to electrode array deployment, as well as on the electrode array and/or mechanical support structure. These markers can be used to assure correct position in the SVC target region by aligning the markers with anatomic landmarks such as the brachiocephalic junction or the right atrium.

Preventing Unintended Stimulation of Cardiac Tissue

An additional feature of the neuromodulation system is one that ensures that the therapeutic neurostimulation does not result in unintended capture of cardiac tissue, that is, capture of right atrial tissue as it meets the SVC. The primary method to prevent unintended capture of cardiac tissue is through proper positioning of the NC as described earlier. Only an incorrectly positioned NC can result in an electrode array that is deployed in contact with atrial tissue. However, an added safety feature in the event that the NC is positioned too close to the right atrium or migrates after placement will next be described as a means to prevent inadvertent atrial capture. In particular, a single test stimulus or series of stimuli prior to initiation of therapeutic neurostimulation to look for inadvertent atrial capture. The test stimuli will be applied using each of the electrode pairs ("test pairs") in the array that are closest to the right atrium. The test stimuli are delivered at high output energy, and synchronous to the ECG in order to assure they are delivered outside of the atrial refractory period. This method can be utilized with any electrode array geometry including those shown in FIGS. 3A through 4B, however an electrode array geometry such as the type shown in FIG. 4A may be particularly useful for this method given its use of additional circumferential distal electrodes, closest to the right atrium. This array provides preferential circumferential coverage to test for inadvertent atrial capture, and may enhance this safety feature.

During delivery of the atrial test stimuli, the clinician monitors the ECG recorded by the neuromodulation system. The physician verifies that there is no capture of atrial tissue as a result of the test stimulus. Once verified, the clinician indicates that the neuromodulator can switch to the next "test pair" in the array and repeats the process, or alternatively, the NM can automatically switch to each of the test pairs. Once all pairs have been evaluated for inadvertent atrial capture, the clinician can then safely begin neurostimulation.

In another preferred embodiment, the NC contains a "floating lead" (described earlier) that extends into the right atrium. In this case, the atrial evoked response can be detected automatically by the NM. The NM will sequence through each of the electrode array "test pairs", and enable the start of therapeutic neurostimulation only if no evoked response is detected as each of the "test pairs" are evaluated.

NeuroCatheter Positioning in the Presence of Existing CRM Leads

In some cases the neurocatheter may be used in patients having permanently implanted CRM devices and the chronic leads that are used with such devices. Such CRM leads typically run from the transvenous entry site of the subclavian vein through the SVC towards the heart. As a result, some patients will have leads existent in the SVC when the NC is deployed. Also, it is conceivable that one or more lead bodies will lie in the target region for parasympathetic and sympathetic nerve capture. The CRM lead bodies, which are covered with silicone or polyurethane insulation, may be free floating in the vessel or attached to the vessel wall and covered with fibrotic or scar tissue (either partially or fully covered), as shown in FIG. 8. Also, in the case of defibrillators and cardiac resynchronization therapy defibrillators, a conductive defibrillation coil electrode may be existent, also shown in FIG. 8. As a result, the NC's electrodes may encounter lead insulation, scar tissue or fibrosis, or the conductive defibrillation coil.

Features of the disclosed electrode array allow target nerve capture despite the presence of CRM leads.

In circumstances where the electrode array will be deployed on top of existing CRM lead bodies or a defibrillation coil electrode, the array of electrodes in combination with the neuromodulation system's previously disclosed automatic response mapping function can allow target nerve capture despite the presence of the CRM lead. This neuromodulation system mapping function can determine the precise electrodes in the array required for capture of the desired parasympathetic and sympathetic cardiac nerves by an algorithm run by the neuromodulator. After placement of the NC in the target SVC region, the neuromodulator initiates stimulation using an electrode pair and looks for HR and BP response, continues to the next pair looking for response gain, and so forth. Early preclinical and clinical data has shown that more than one electrode pair can capture the target nerves. Therefore, in the event that CRM lead insulation, fibrosis, or a defibrillation coil electrode impact the ability to capture with one electrode pair, adjacent pairs in all directions provide added options for target nerve response. Also, during the automatic response mapping function, the impedance between electrode pairs is measured during each mapping step to avoid pairs that have very high impedance (which would indicate the pair is deployed in the presence of lead insulation) or pairs that have very low impedance (which would indicate the pair is deployed in the presence of a conductive defibrillation coil electrode). This impedance checking step ensures that the automatic response mapping algorithm only tests electrode pairs that have the potential for target nerve capture, and quickly eliminates pairs that may be deployed in the presence of CRM leads.

Exemplary Electrodes

Additional details of the electrode arrays shown in FIGS. 3A-4B will next be described. In general, the electrode arrays and their associated supports may be elements of a catheter that includes a catheter body, the support structure on a distal portion of the catheter body, and the electrode array on the support structure. As disclosed in the prior applications referenced herein, electrodes in the electrode array are electrically coupled to a neurostimulator that energizes the electrodes using stimulation parameters selected to capture the target nerve fibers and to achieve the desired patient effect.

In a preferred arrangement, the electrode array includes a flexible substrate. The substrate is preferably formed of an insulating material, such as a polymer (including silicone, polyurethanes, polyimide, and copolymers) or a plastic. Thus electrode surfaces will be exposed on one side of the array (the side intended to be against the SVC wall) and insulated by the substrate on the other side of the array in order to capture target nerves through the SVC wall with efficient stimulation energies, and avoid collateral stimulation through the blood pool. Where the neurocatheter is to be used for acute use (typically 36-72 hours, but in general less than 7 days), the electrodes may be constructed of a variety of alloys, including stainless steel, titanium, cobalt chromium, and platinum alloys.

Figure 4A:
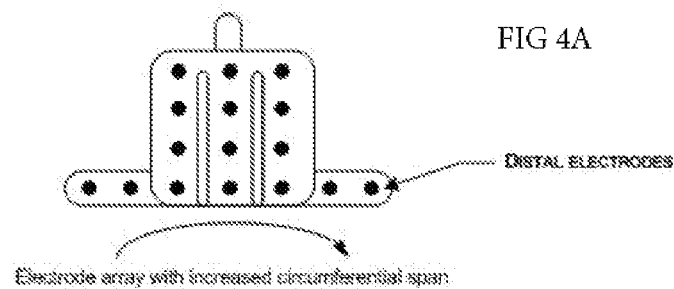
Figure 4B:
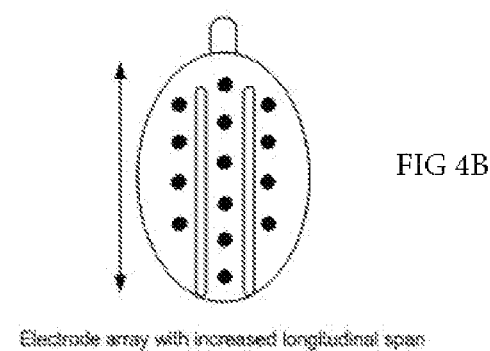

The electrodes are arranged on the substrate in a variety of geometries in order to provide the desired stimulation "coverage region" (both circumferentially and longitudinally). FIG. 2 shows a preferred electrode array on substrate 8. The array is arranged in a rectangular shape that contains a 4×4 array of electrodes 14 for a total of 16 electrodes. The drawing shows what would be the posterior face of the electrode array within the SVC (i.e. the face that contacts the posterior region of the wall of the SVC lumen). In this arrangement, the substrate has a geometry resembling a fork—with a plurality of parallel, longitudinally extending tines or fingers 16 laterally separated from one another at their distal ends. Linear arrangements of electrodes are disposed on each such finger 16. Other preferred embodiments include other geometric arrays that contain from 4 to 32 electrodes, and that can be arranged in, or on substrates having, rectangular, circular (FIG. 3), oval (FIG. 4B) or irregular configurations, such as the one shown in FIG. 4A. As shown, these embodiments can likewise include longitudinally-extending fingers 16 with linear arrangements of electrodes disposed on them. These can be arranged to provide an effective coverage area that spans greater circumferential area as depicted in FIG. 4A, or greater longitudinal area, as depicted in FIG. 4B.

Independent of geometric shape, each electrode in the array will be spaced from adjacent electrodes by a longitudinal distance, $d_L$, and a circumferential distance, $d_C$. The spacing between electrodes is chosen to optimize capture of target nerves, and may be from 1 to 10 mm, typically 5 mm, and the longitudinal and circumferential spacing may be equal or may differ.

In some embodiments, the array might include a greater circumferential expanse of electrodes in the distal electrodes (see, e.g. FIG. 4A), which in use are positioned closest to the right atrium. Where the neurocatheter is introduced using a femoral approach, the most proximal electrodes in the array will lie closest to the atrium and might be provided with a greater circumferential expanse. This arrangement can facilitate positioning methodologies that allow safe positioning of the array so as to avoid the risk of atrial capture, as disclosed above.

The electrodes can be constructed on the substrate using a variety of manufacturing techniques, including subtractive manufacturing processes (such as mechanical removal by machining or laser cutting), additive processes (such as laser sintering, deposition processes, conductor overmolding), or combinations (such as printed circuit technology with additive plating). When assembled on the catheter, the electrodes and substrate (where used) will be attached to or manufactured on a mechanical support structure (described below) having features for biasing the electrodes against the vascular wall and, optionally, supporting the distal end of the neurocatheter against the vascular wall or spaced from the vascular wall.

Mechanical Support Structure for the Electrode Array

In order to capture target nerves through the SVC wall with efficient stimulation energies, secure engagement of the electrodes against the SVC wall is desired. Therefore, the catheter includes a support structure or structures that provide mechanical force to press the electrode surfaces against the SVC wall once deployed. Additionally, the support structure securely but reversibly (at least in the case of an acute device) anchors the catheter to prevent its migration within the vasculature. The support structures are constructed of a variety of shape memory alloys, such as nickel-titanium, or other alloys that would be mechanically positioned by mechanisms in the catheter body. Where the substrate described above is used to form the array, the support structures may be integral with the substrate, or coupled to the substrate.

Figure 5:
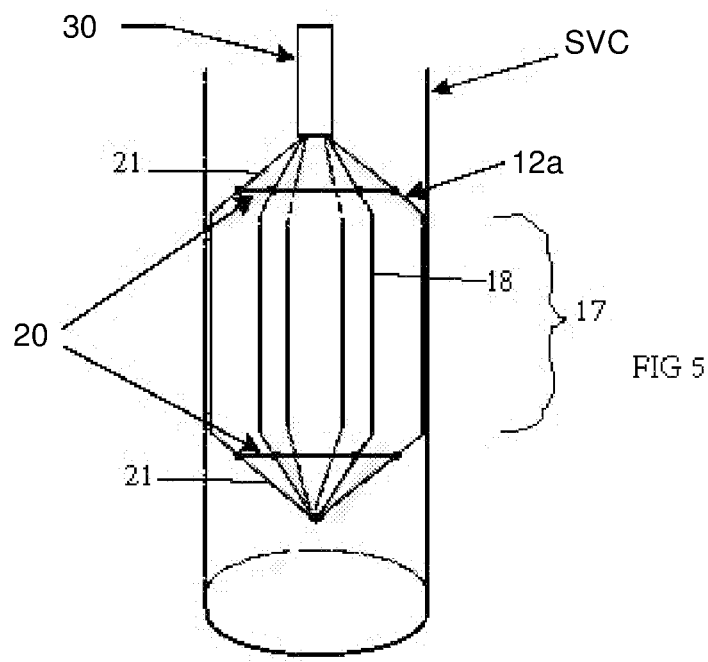
Figure 6:
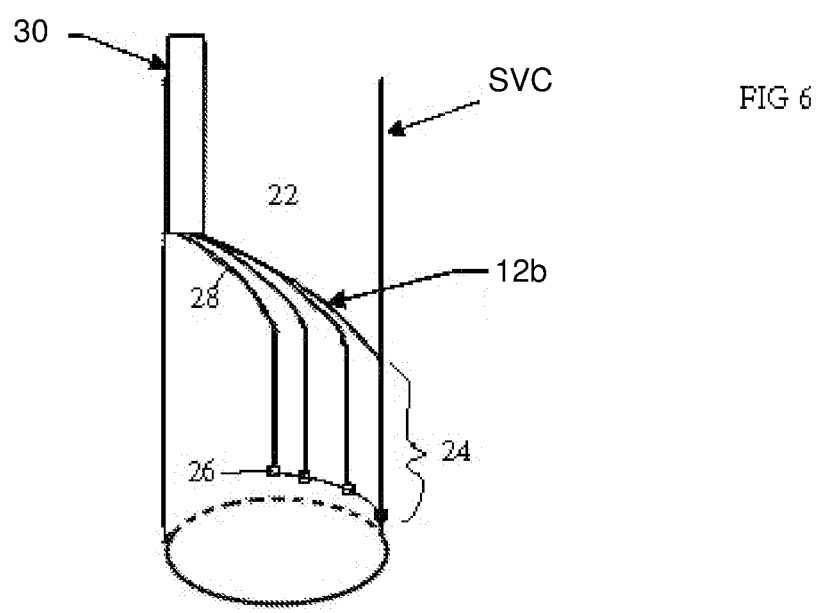

Preferred embodiments for the support structures include a full cylindrical configuration, shown in FIG. 5, a fork configuration, shown in FIG. 6, and a partial cylindrical configuration, shown in FIG. 7. In all of these configurations, the electrode array, which is only required to cover a portion of the circumference of the SVC, will be attached to the support structure. In FIGS. 5 through 7, the electrode array is not shown to allow the support structure to be more easily seen. In preferred embodiments, the electrode arrays with the associated insulative substrates disclosed above are used.

In use, the support structure is radially expanded at the target electrode site within the vasculature using known means. For example, the support structure with the attached electrode array may be compressed within a deployment sheath for advancement through the vasculature, and then released from the deployment sheath at the target electrode site. The support structure self expands at the target site, or is actively expanded using a balloon or other expansion structure, positioning and biasing the electrodes against the vessel wall.

The full cylindrical support structure 12a (FIG. 5) includes a cylindrical portion 17 formed of a plurality of parallel longitudinally-extending support elements 18. When the support structure is expanded within the vasculature, the support elements of the cylindrical portion contact the vessel wall. The electrode array is carried on the cylindrical portion of the support structure, and in particular is mounted to a subset of the longitudinally-extending support elements that expands towards the target SVC wall region. For example, each of the longitudinal fingers 8 of the substrate shown in FIG. 2 may extend along four adjacent longitudinally-extending elements 18 of the cylindrical part of the support structure. The opposed longitudinally-extending support elements forming the cylindrical portion contact the opposed portion of the vessel wall, such that the entire array of longitudinal support elements aid in securing the electrode array to the vessel wall.

In the FIG. 5 arrangement, the support structure biases the distal end of the neurocatheter's body 30 towards the center of the SVC lumen as shown. This central positioning of the neurocatheter body 30 and deployed structure for the electrode array creates a uniform shape that results in central, more uniform laminar blood flow patterns to prevent thrombosis. In this central design, adequate space does exist through openings in the support structure on either side of the catheter body to allow other catheters or devices to be inserted through the SVC when needed. The FIG. 5 embodiment includes cross members 20 to provide circumferential structure. These cross members are positioned at the distal and, optionally, proximal ends of the support structure between struts 21 that angle inwardly from the longitudinally-extending members. This places the cross members struts away from the vessel wall when the structure is fully deployed as shown in FIG. 5, rather than between the longitudinally-extending members of the cylindrical portion, thus leaving the spaces between the longitudinally-extending members 18 (and thus the spaces between the longitudinal columns of electrodes on those members) clear. Where the electrodes are being deployed in an area of the SVC where cardiac rhythm management (CRM) leads reside, these spaces give room for the columns of electrodes on the neurocatheter to circumferentially shift around existing lead bodies and into contact with an adjacent portion of the vessel wall, as will be discussed in further detail in connection with FIG. 8.

Another embodiment of a support structure is the fork support structure 12b shown in FIG. 6. This embodiment includes a series of longitudinal members 22. These members have distal sections 24 running in parallel to one another and including free distal ends 26, similar to tines of a fork. Proximal sections 28 extend from the neurocatheter body 30 to the proximal ends of the distal sections 24. The electrodes are positioned along the distal sections (with or without the substrate arrangements described above). When released from a deployment sheath, the fork structure expands to position each of the distal sections 24 and their associated electrodes against the SVC wall. This arrangement minimizes material and facilitates better compression into the deployment sheath to minimize delivery diameter. By applying mechanical forces on one side of the wall (in contrast with the forces applied around the cylinder in the FIG. 5 embodiment), the distal portion of the neurocatheter body 30 is biased towards the portion of the SVC wall opposite to the portion against which the electrodes are biased, as shown in FIG. 6. This leaves maximum cross-sectional space between the longitudinal members, allowing other catheters or devices to be inserted through the SVC, as would be typically required for patients in acute hospital care. In addition, by having the neurocatheter body positioned against the vessel wall, central blood flow disruption can be minimized to prevent thrombosis. Also, like the full cylindrical structure and as discussed further in connection with FIG. 8, the individual longitudinal members 22 leave space between the longitudinal columns of electrodes so that if, upon expansion of the support structure, the longitudinal columns collide with resident CRM leads within the SVC, the columns can shift into contact with SVC wall space adjacent to the CRM leads.

The support structure 12c of the FIG. 7 embodiment combines features of the FIGS. 5 and 6 embodiments by combining a partially cylindrical structure with opposing mechanical support legs 22a (e.g. two or more legs of the type used in the FIG. 6 embodiment). In this configuration, a partial cylinder 17a of support elements 18a carrying the electrode array is secured against the SVC wall on one side of the deployed support structure, and a number of opposing elements or legs 22a expands on the other side of the support structure to provide an equal and counteracting force against the SVC wall opposite the target region. The partial cylindrical structure may incorporate features of the FIG. 5 support structure, but will extend less than 360 degrees around the circumference of the SVC. The number of opposing legs 22a would preferably be 2, but more legs, up to 6, can be included. In this arrangement the distal portion of the neurocatheter body 30 is again biased towards the center of the SVC, as in the full cylindrical configuration. In a variation of this embodiment, the support legs 22a shown in FIG. 7 may be positioned against the blood vessel wall on one side of the blood vessel, and the members 24 of the fork-like structure of the FIG. 6 embodiment (with the electrode array thereon) positioned on the opposed portion of the blood vessel wall.

Electrode Array Use in the Presence of Existing CRM Leads

As noted above in connection with FIG. 8, in some cases the neurocatheter may be used in patients having permanently implanted CRM devices and the chronic leads that are used with such devices. The mechanical layout and design can array allow target nerve capture despite the presence of CRM leads. In particular, the mechanical layout and design of the neurocatheter electrode array and support structure facilitate engagement in the presence of CRM lead bodies. A critical and common feature of both the fork and cylinder support structures is that they have parallel elements with openings where engaged to the target SVC vessel wall. These openings provide the most flexibility when engaging against the vessel wall in the presence of chronic CRM leads, by allowing the electrodes to engage against irregular surfaces presented by attached lead bodies and the ability to have the longitudinal electrodes engage the SVC wall by moving between or around free floating leads to engage active tissue.

It should be recognized that a number of variations of the above-identified embodiments will be obvious to one of ordinary skill in the art in view of the foregoing description. Moreover, it is contemplated that aspects of the various disclosed embodiments may be combined to produce further embodiments. Accordingly, the invention is not to be limited by those specific embodiments and methods of the present invention shown and described herein. Rather, the scope of the invention is to be defined by the following claims and their equivalents.

All prior patents and applications referred to herein, including for purposes of priority, are incorporated by reference for all purposes.

I claim:

1. A method for positioning an electrode array of a neuromodulation catheter at a target circumferential position along a posterior wall of a superior vena cava located within a patient body, the method comprising:
   providing a neuromodulation catheter including a catheter body, an electrode array on a distal portion the catheter body, and a marker on the catheter body, the marker positioned to face a mid-anterior position when the electrode array is at the target circumferential position along the posterior wall;

advancing the catheter to a target longitudinal position within the superior vena cava, the marker remaining outside the patient body;

with the patient in a supine position, orienting the marker perpendicular to the patient body.

2. The method according to claim 1, wherein the marker is a stripe.

3. The method of claim 1, wherein when the marker is oriented perpendicular to the patient body, a plurality of the electrodes extend in a longitudinal direction within the blood vessel.

4. The method of claim 1, wherein when the marker is oriented perpendicular to the patient body, a plurality of the electrodes extend in a circumferential direction within the blood vessel.

* * * * *